(12) United States Patent
Godfroy et al.

(10) Patent No.: US 12,246,104 B2
(45) Date of Patent: Mar. 11, 2025

(54) FAR UV-C LIGHT DEVICE

(71) Applicants: Thomas J. Godfroy, Huntsville, AL (US); Robert V. Albertson, Mound, MN (US); Kurt R. Knappen, Galesville, WI (US)

(72) Inventors: Thomas J. Godfroy, Huntsville, AL (US); Robert V. Albertson, Mound, MN (US); Kurt R. Knappen, Galesville, WI (US)

(73) Assignee: ULTRA-VIOLET SOLUTIONS, LLC, Huntsville, AL (US)

( * ) Notice: Subject to any disclaimer, the term of this patent is extended or adjusted under 35 U.S.C. 154(b) by 446 days.

(21) Appl. No.: 17/699,458

(22) Filed: Mar. 21, 2022

(65) Prior Publication Data

US 2022/0305158 A1    Sep. 29, 2022

Related U.S. Application Data

(60) Provisional application No. 63/164,707, filed on Mar. 23, 2021.

(51) Int. Cl.
*A61L 2/10*     (2006.01)

(52) U.S. Cl.
CPC .............. *A61L 2/10* (2013.01); *A61L 2202/11* (2013.01); *A61L 2202/16* (2013.01)

(58) Field of Classification Search
CPC .... A61L 2/10; A61L 2202/11; A61L 2202/14; A61L 2202/16
See application file for complete search history.

(56) References Cited

U.S. PATENT DOCUMENTS

| | | | |
|---|---|---|---|
| 7,888,657 B1* | 2/2011 | Zadro | A61L 2/10 250/455.11 |
| 11,007,292 B1* | 5/2021 | Grenon | F21V 11/08 |
| 11,469,093 B2* | 10/2022 | Taniguchi | A61L 2/10 |
| 2009/0256460 A1* | 10/2009 | Allen | H01J 61/52 313/643 |
| 2022/0047743 A1* | 2/2022 | Miller | A61L 2/10 |

* cited by examiner

*Primary Examiner* — David E Smith
(74) *Attorney, Agent, or Firm* — Richard John Bartz

(57) ABSTRACT

A Far UV-C light device has a Far UV-C lamp located within a housing emitting a Far UV-C light having a wavelength of 222+/−1 nm for destroying pathogens. A handle connected with a body to a housing allows the Far UV-C device to be hand held and moved to a selected location. The handle is attached to a battery that provides electric energy that excites the Far UV-C lamp to emit Far UV-C light.

6 Claims, 6 Drawing Sheets

FAR UV-C LIGHT DEVICE

CROSS REFERENCE TO RELATED APPLICATION

This application claims the priority of U.S. Provisional Application Ser. No. 63/164,707 filed Mar. 23, 2021.

FIELD OF THE INVENTION

The invention relates to hand held Far UV-C light devices for eradicating and destroying pathogens on surfaces, objects and the epidermis of a human.

BACKGROUND OF THE INVENTION

Germicidal ultraviolet light with a wavelength of 254 nanometers (254 nm) is a long time standard for germicidal light fixtures. The germicidal light is identified as Far UV-C light that is emitted from a Far UV-C light source, such as a lamp or light emitting diodes. The Far UV-C light sterilizes environments by eradicating and neutralizing pathogens including viruses, bacteria, spores, and yeasts. Portable UV-C wands and stationary products have UV-C light lamps that emit UV-C light to destroy or neutralize pathogens. Examples of germicidal UV-C light devices and UV-C lamps are disclosed in the following U.S. patents and U.S. patent application publications.

U.S. Pat. No. 4,952,369 discloses a hand held ultra-violet flashlight for sterilizing objects and surfaces. An ultra-violet lamp enclosed in a housing is connected to batteries operable to activate the lamp to generate ultra-violet light in sufficient intensity to disinfect objects at relatively short distances. A handle is extended from the housing for hand holding the portable flashlight.

U.S. Pat. No. 6,971,939 discloses a method of making an excimer lamp having a glass cylindrical tube surrounding a chamber for a gas. A first cylindrical inner electrode is deposed on the inside surface of the tube. A second electrode is on the outside cylindrical surface of the tube. At least one of the electrodes can be in the shape of a mesh or grid. The electrodes are described as "aluminum or the like." The electrodes are deposed on the lamp surfaces by deposition techniques including chemical vapor deposition, physical vapor deposition, screen printing and sputtering. A photolithography process that etches the mesh on the surface of the lamp can also be used. A protective layer covers the electrodes to prevent oxidation of the electrodes during lamp operation. The method includes covering the electrode with a protective layer that separates the electrodes from the environment adjacent to the excimer lamp.

U.S. Pat. No. 7,714,511 discloses an excimer lamp having a vessel. A wire mesh electrode is arranged on the top surface of the vessel. A second wire mesh electrode is on the bottom surface of the vessel. The electrodes are formed by vacuum evaporation.

U.S. Pat. No. 7,834,335 discloses a hand held sterilization device having a cover housing accommodating a light housing and a battery. The cover housing serves as a handle for holding and moving the device across a target surface to sterilize or disinfect the surface. A UV-C light source on the light housing comprises a UV-C lamp or light emitting diodes that emit UV-C light at about 240 nm to 290 nm that destroys microorganisms.

U.S. Pat. No. 7,859,191 discloses a silica glass vessel filled with xenon gas. Electrodes are on opposite sides of the vessel. The electrodes are formed by paste-coating the vessel with metallic electrode material or by means of circuit printing operations.

U.S. Pat. No. 9,657,177 discloses a coating with a pigment configured to reflect UV-C light. The coating includes an inorganic material. Aluminum oxide particles and magnesium particles are examples of UV-C light reflecting substances.

U.S. Patent Application Publication No. 2011/0156581 discloses a quartz glass lamp. Electrodes are metal plates fixed tightly to opposite outer surfaces of the lamp. A mixture of krypton and chlorine gas fills the discharge chamber. An excimer light having the wavelength of 222 nm is emitted.

U.S. Patent Application Publication No. 2016/0225604 discloses an excimer lamp comprising a quartz glass tube. A coiled inner tungsten electrode is located axially within the tube chamber. A net-like outer electrode is located on the outer surface of the tube. The outer electrode is a plurality of wires fixed to the tube. A rare gas, such as xenon gas, argon gas or krypton gas, is within the tube.

U.S. Patent Application Publication No. 2020/0215210 discloses a Far UV-C light device for eliminating pathogens on localized areas and air surrounding a surface. The device includes a hand grip for holding and moving the device relative to a surface. The device has a Far UV-C light source with a wavelength between 200 nm and 230 nm. The light source includes an excimer lamp or light emitting diodes that emits illumination having a wavelength of 222 nm. Rechargeable batteries are utilized to energize the light source.

SUMMARY OF THE INVENTION

The UV-C light device of the invention utilizes Far UV-C light to sanitize surfaces and objects by subjecting the surfaces and objects to Far UV-C light. The Far UV-C light device is hand held and portable and utilized to sanitize selected surfaces, air surrounding the surfaces and objects on the surfaces. The UV-C light device has a light wavelength that is safe for humans while eliminating pathogens. The Far UV-C light device has a Far UV-C light source located within a housing. The Far UV-C light source emits UV-C light having a light wavelength or spectrum of between 210 nm and 230 nm. The optimum light wavelength is 222+/−1 nm to effectively destroy or neutralize pathogens including viruses, bacteria and microorganisms. A handle connected to the housing supports a battery operable to supply electric energy to activate the Far UV-C light source. An electric circuit transmits electric energy from the battery to the Far UV-C light source. The electric circuit includes a transformer operable to provide high voltage to the Far UV-C light source to activate the Far UV-C light source to emit Far UV-C light.

An embodiment of the Far UV-C device comprises a handle having a first end and a second end opposite the first end. A body joined to the first end of the handle is secured to a housing. The housing includes a wall surrounding an interior chamber and an opening to the exterior environment. A Far UV-C light source, such as a Far UV-C lamp or light emitting diodes, located in the interior chamber of the housing is operable to emit Far UV-C light having a light wavelength of 222+/−1 nm toward the opening of the housing to destroy pathogens located adjacent the housing. A light reflector comprising a concave member located in the interior chamber of the housing reflects Far UV-C light from the Far UV-C light source toward the opening of the housing. A d.c. battery attached to the second end of the handle is operatively connected to an electric circuit. The electric circuit includes a transformer for supplying a voltage to a Far UV-C light source to activate the Far UV-C light source to emit the Far UV-C light.

DESCRIPTION OF THE FAR UV-C LIGHT DEVICE

Figure 1:
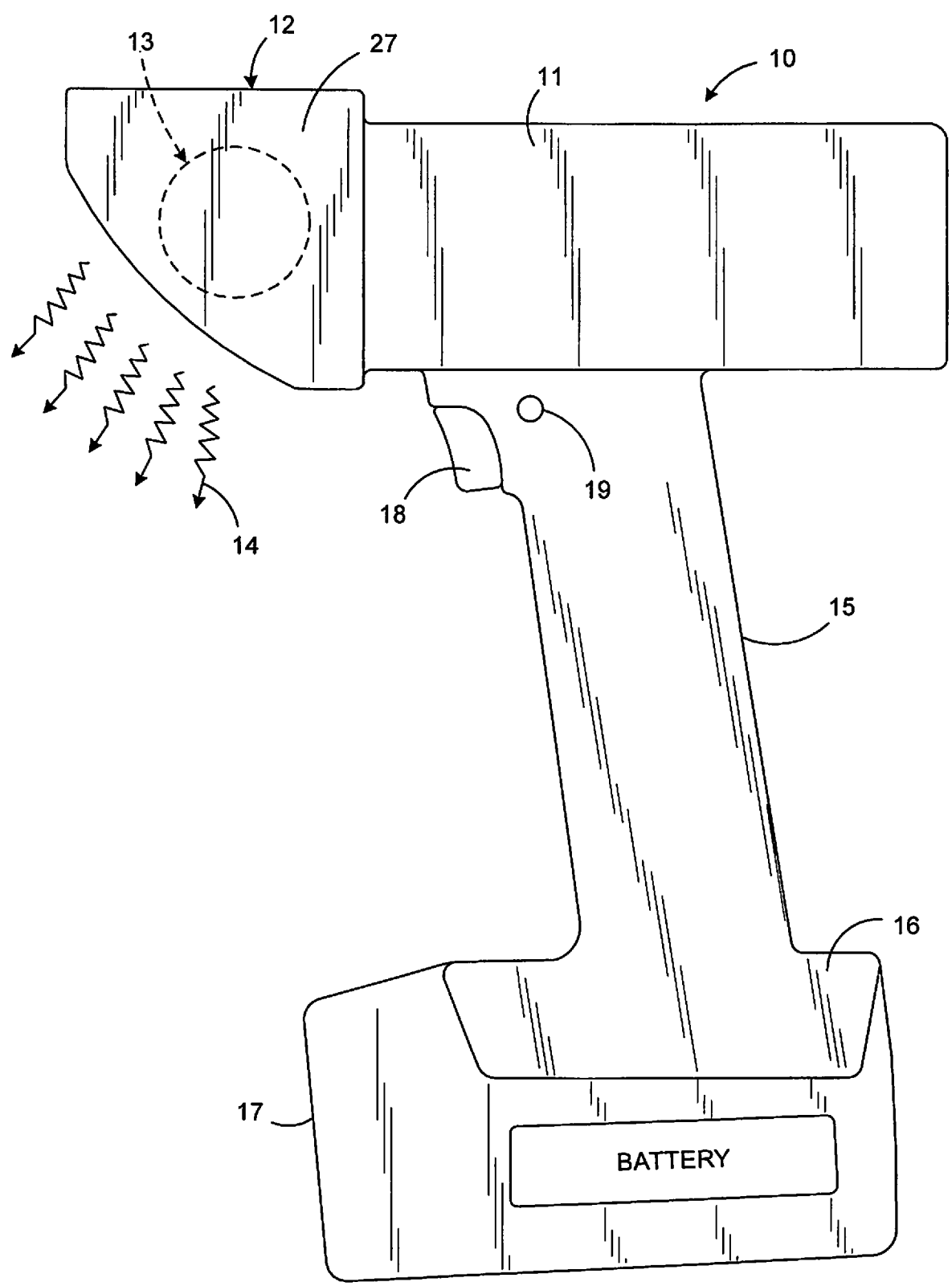
FIG. 1 is a right side view of a Far UV-C light device of the invention.

The far UV-C light device 10, shown in FIG. 1, emits a Far UV-C light wavelength or spectrum between 210 nm and 230 nm for use as a germicidal light to sterilize, eradicate or cause neutralization of pathogens including viruses, bacteria and microorganisms. Device 10 is hand manipulated to be moved and placed in selected locations to sterilize air, surfaces and objects. Device 10 has a body 11 supporting a housing 12. A Far UV-C light source 13 located within housing 12 is operable to generate Far UV-C light or light radiation 14 into the environment. The Far UV-C light source 13 includes a Far UV-C lamp or light emitting diodes. A handle 15 joined to body 11 is mounted on a d.c. battery 17, known as a battery pack. Handle 15 has a battery holder 16 releasably attached to battery 17. The handle 15 has a trigger 18 operatively connected to an electric circuit for transmitting electric power from battery 17 to Far UV-C light source 13. A locking member 19 located adjacent trigger 18 is operable to retain trigger 18 in a position to maintain the electric circuit in an ON condition with the trigger 19 is not manually operated.

Figure 4:
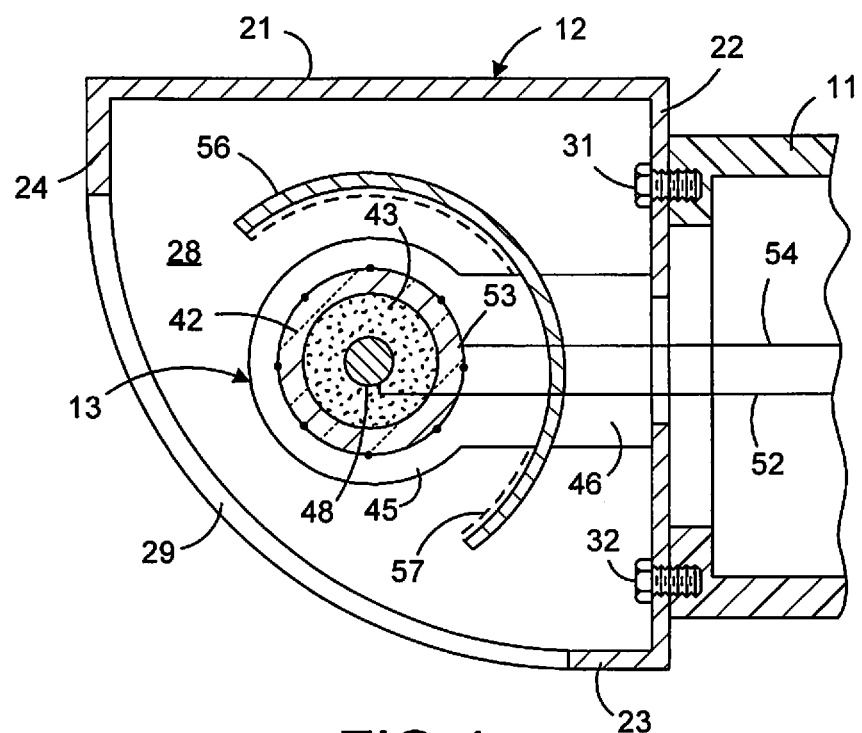
FIG. 4 is a sectional view taken along the line 4-4 of FIG. 2.

Housing 12 is a box-shaped sheet metal or plastic member having a top wall 21 jointed to an upright back wall 22 and front wall 24. Back wall 22 is jointed to a bottom wall 23. End walls 26 and 27 are joined to walls 21, 22, 23 and 24. The walls 21 to 24, 26 and 27 surround an interior chamber 28 accommodating the Far UV-C light source 13, shown as a cylindrical lamp. The light source can have an elongated square, rectangular or flat shape. Housing 12 has a front opening 29 to interior chamber 28 allowing Far UV-C light emitted by the Far UV-C light source 13 to be transmitted to a selected location. As shown in FIG. 4, fasteners 31 and 32, shown as bolts, secure back wall 22 to body 11. Other types of connecting structures can be used to secure housing 12 to body 11.

Figure 5:
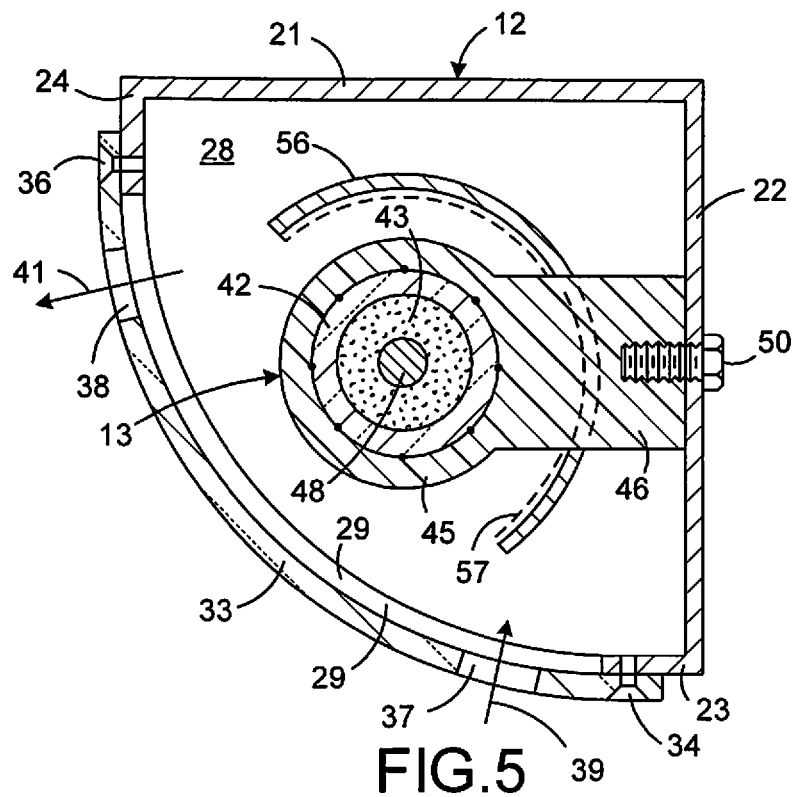
FIG. 5 is a sectional view of FIG. 3 with an ultraviolet transparent glass window on the housing of the Far UV-C light device.
Figure 6:
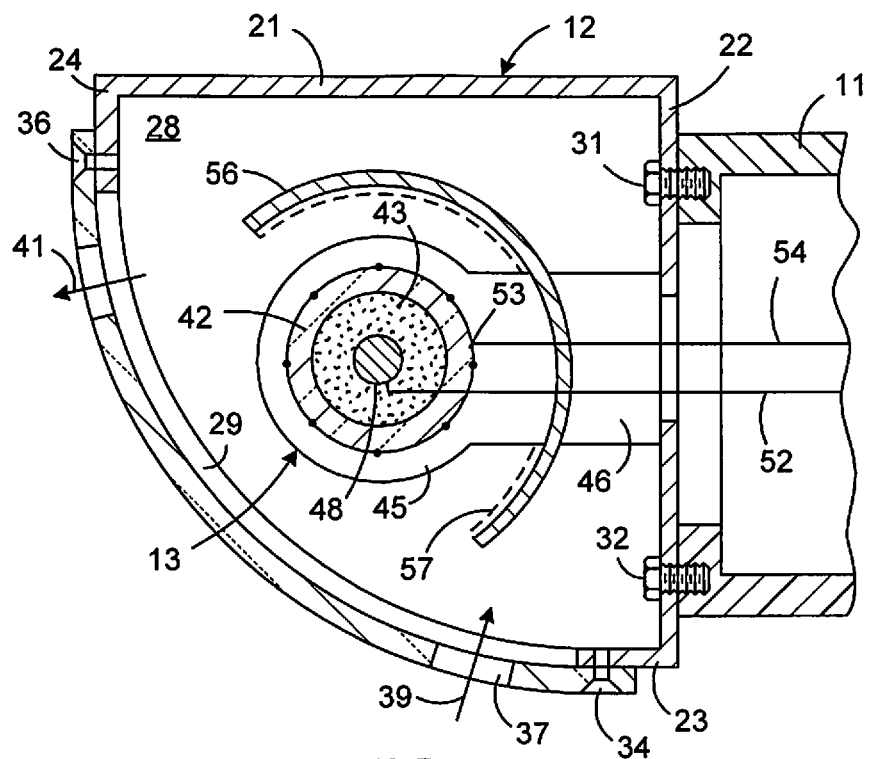
FIG. 6 is sectional view of FIG. 4 with an ultraviolet transparent glass window with holes on the housing of the Far UV-C light device.
Figure 7:
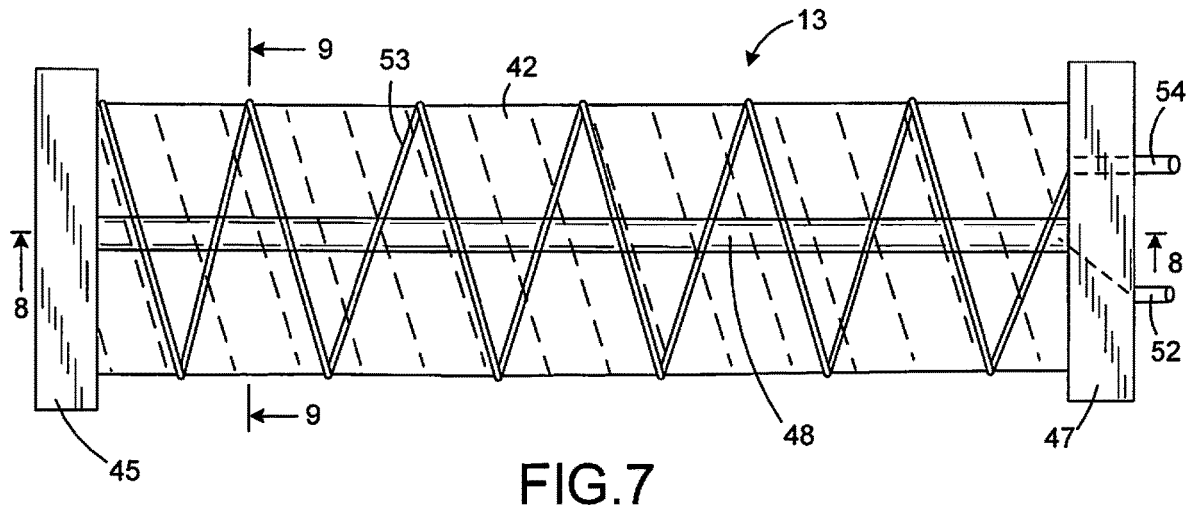
FIG. 7 is a side elevational view of the Far UV-C light source of the Far UV-C light device shown in FIG. 2.
Figure 8:
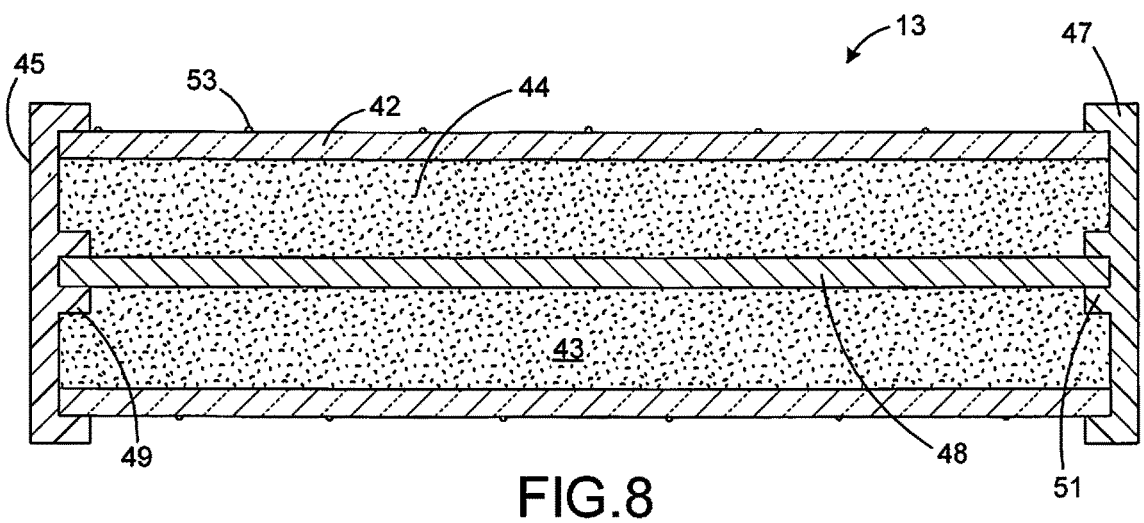
FIG. 8 is a sectional view taken along the line of 8-8 of FIG. 7.
Figure 9:
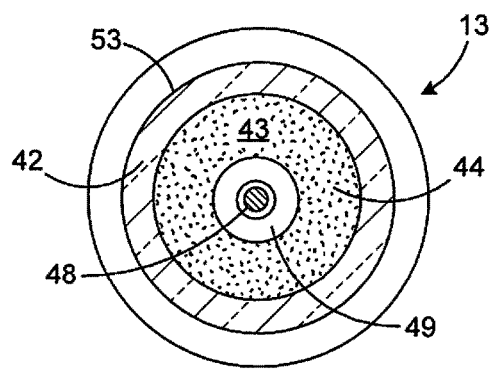
FIG. 9 is a sectional view taken along the line 9-9 of FIG. 7.

Proceeding to FIGS. 5 and 6, a window 33 comprising a convex ultraviolet transparent glass pane, such as a quartz glass pane, extends over opening 29 and housing 12. Fasteners 34 and 36, shown as bolts, secure window 33 to bottom wall 23 and top wall 36. Alternative fasteners can be used to secure window 33 to housing 12. Window 33 has a number of apertures or holes 37 and 38 to allow air, shown by arrows 39 and 41, to flow through chamber 28. The air flowing through chamber 28 cools the Far UV-C lamp 13 and housing 12. A screen type window can be used to cover opening 29 of housing 12.

The Far UV-C light source 13, shown in FIGS. 2 and 7 to 9, comprises a linear ultraviolet transparent cylinder or tube 42 having an internal chamber 43 containing chemically inactive gases 44. An example of the gases 44 is a mixture of krypton and chlorine gas that when subjected to electric energy emits Far UV-C light having a wavelength of 222+/−1 nm. Other gas mixtures, such as an argon and neon gas mixture, can be confined to chamber 43. A first electrode 48 is located along the longitudinal axis of chamber 43. The electrode 48 is a metal rod having ends anchored to end members or caps 45 and 47. Electrode 48 comprises an electrical conductor, such as a copper rod. An electrical conductor 52 extended through end member 47 connects electrode 48 to the electric circuit within body 11. End members 45 and 47 have cup-shaped retainers 49 and 51 accommodating opposite ends of electrode 48. End members 45 and 47 are sealed on opposite ends of tube 42 to confine the gas mixture 44 to the chamber 43 of tube 42. As shown in FIGS. 3 and 4, a support 46 joined to end member 45 extends rearward to back wall 22 of housing 12. A fastener 50 secures support 46 to back wall 22. End member 47 is also joined to a support secured to back wall 22 identical to support 46. The supports hold Far UV-C light source 13 transversely in chamber 28 of housing 12 in a spaced relation relative to the walls of housing 12 and facing the length of opening 29. Other structures can be used to support the Far UV-C light source 13 on housing 12.

A second metal electrode 53 is located on the outer cylindrical surface of tube 42. Electrode 53 is a continuous electrical conductor, shown as a metal wire mesh, attached to tube 42. The electrode 53 is applied to tube 42 with a plasma spraying process that impacts the metal wire mesh in the outer surface of tube 42 as a continuous metal electrical conductor having uniform thickness. The plasma spraying process does not damage or distort the glass of tube 42. Other methods can be used to deposit the electrode 53 on tube 42. These methods include chemical vapor deposition, screen printing and photolithography etching. A protective layer covers the electrode 53 to prevent oxidation during operation of the Far UV-C light source 13. An electrical conductor 54 extended through end chamber 47 connects electrode 53 to the electric circuit within body 11 and handle 15.

Figure 2:
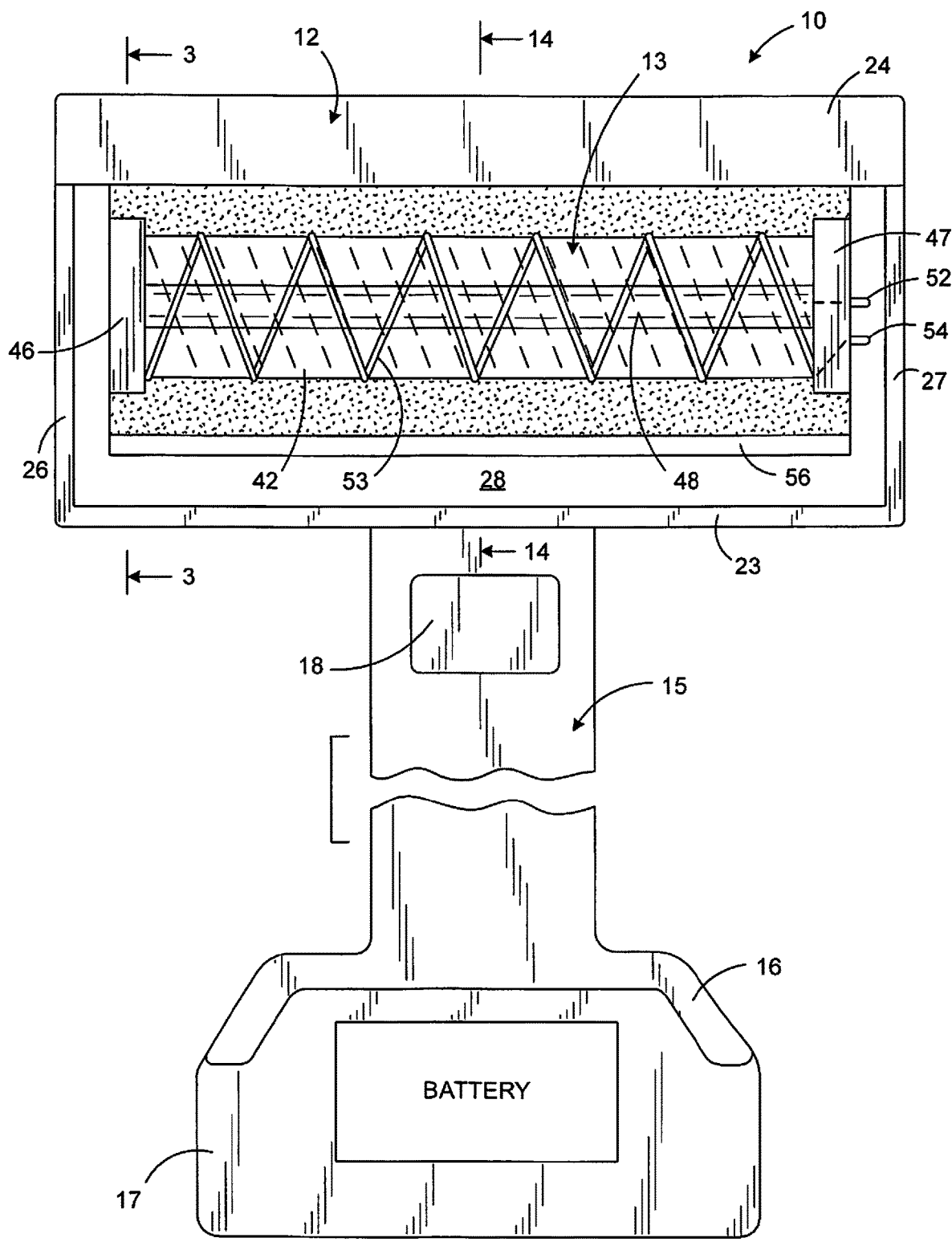
FIG. 2 is an enlarged foreshortened front elevational view of the Far UV-C light device of FIG. 1.
Figure 3:
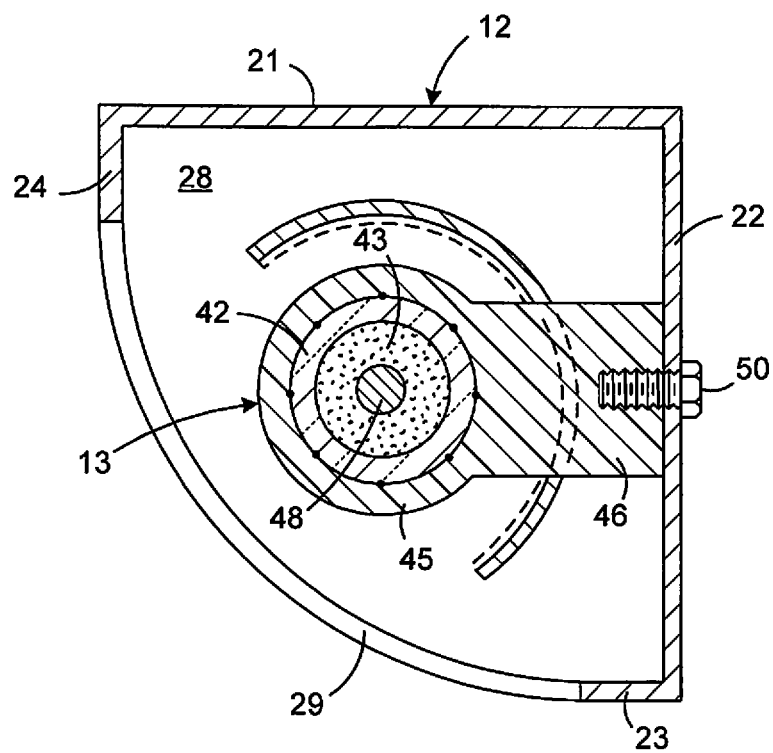
FIG. 3 is a sectional view taken along the line 3-3 of FIG. 2.

As shown in FIGS. 2, 3 and 4, a Far UV-C light reflector 56 located in chamber 28 between Far UV-C light source 13 and top wall 21 and back wall 22 of housing 12 reflects Far UV-C light emitted from Far UV-C light source 13 toward opening 29 of housing 12. Reflector 56 focuses the emitted light into a narrow area in front of device 10. Reflector 56 has a semi-circular shaped member or sleeve with a convex surface concentric with the tube 42 of Far UV-C light source 13. Reflector 56 can have a parabolic form with an inside surface spaced from Far UV-C light source 13 to reflect Far UV-C light emitted from Far UV-C light source 13 toward opening 29 of housing 12. A coating 57 of Far UV-C light reflecting material is on the convex surface of reflector 56. Aluminum oxide and magnesium oxide are examples of the light reflecting materials included in coating 57. Opposite ends of reflector 56 are attached to supports 46 to hold the reflector 56 adjacent to Far UV-C light source 13. The reflector 56 can be a polished aluminum member having a semi-circular shape.

Figure 10:
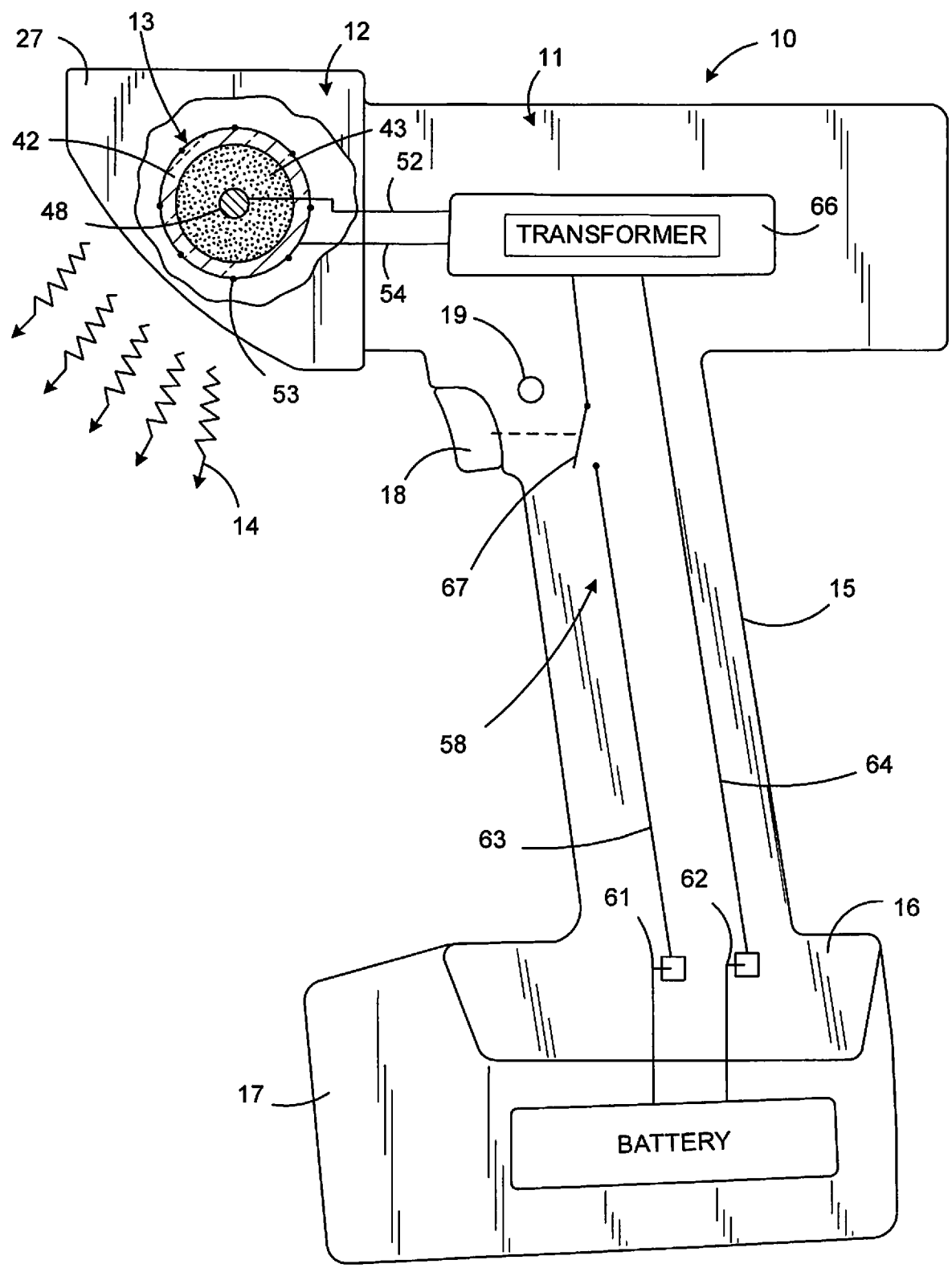
FIG. 10 is an outline of the Far UV-C device with the electric operating circuit and a d.c. battery for the Far UV-C light source.

Proceeding to FIG. 10, the electric system 58 incorporated within the body 11 and handle 15 provides the electric energy for exciting the gas 44 confined to internal chamber 43 of tube 42 to emit Far UV-C light. The electric power source is the d.c. battery 17 that is releasably attached with battery holder 16 to the lower end 59 of handle 15. Battery 17 is a rechargeable d.c. battery with plus and minus terminals 61 and 62 releasably connected to electric conductors 63 and 64 located in handle 15. 1.5 to 48 volt batteries can be used to supply electric energy. Electric conductors 63 and 64 are also connected to a transformer 66. Transformer 66 wired to electrode 48 and mesh electrode 53 provides voltage to electrode 48 that excites the gas 44 in internal chamber 43 of Far UV-C light source 13 to emit Far UV-C light. A switch 67 operated ON and OFF by trigger 18 controls the operation of transformer 66. Trigger 18 is manually moved by the operator holding the device 10.

While the Far UV-C light device has been shown and described as a preferred embodiment, it is to be understood that the Far UV-C light device is not limited to the disclosed embodiment. The invention of the Far UV-C light device includes various modifications and equivalent arrangements of structures included within the scope of the appended claims.

The invention claimed is:

1. A UV-C light device comprising:
a tubular upright handle having a first end and a second end opposite the first end,
a body joined to the first end of the handle, said body having an end,
a housing having a top wall, a back wall and a front wall surrounding an interior chamber, said front wall having an opening to the external environment,
at least one fastener attaching the body to the back wall of the housing,
a UV-C lamp located in the interior chamber of the housing operable to emit UV-C light having a wavelength of 222+/−1 nm toward the opening of the housing,
supports holding the UV-C lamp on the back wall of the housing,
a UV-C light reflector located in the interior chamber of the housing between the back wall of the housing and the UV-C lamp for reflecting UV-C light toward the opening in the housing,
a d.c. battery,
a holder on the second end of the handle for releasably attaching the battery to the second end of the handle, and
an electric circuit located in the handle and the body operatively connected to the d.c. battery and the UV-C lamp for supplying electric energy from the d.c. battery to the UV-C lamp whereby the UV-C lamp emits UV-C light having a wavelength of 222+/−1 nm toward the opening of the housing.

2. The UV-C light device of claim 1 wherein:
the UV-C lamp comprises an ultraviolet transparent glass tube with an interior chamber and an exterior surface,
a chemically inactive gas confined to the interior chamber of the tube,
a first electrode located in the interior chamber of the tube,
a second electrode located on the exterior surface of the tube, and
said electric circuit connected to the first electrode and the second electrode providing electric energy to the first electrode for exciting the gas confined in the interior chamber of the tube to emit UV-C light having a wavelength of 222+/−1 nm.

3. The UV-C light device of claim 2 wherein:
the gas confined to the interior chamber of the tube is a mixture of krypton and chlorine gas.

4. The UV-C light device of claim 2 wherein:
the second electrode is applied to the exterior surface of the tube by a plasma spraying process.

5. The UV-C light device of claim 1 including:
an ultraviolet transparent window located over the opening of the housing, and
fasteners securing the window to the housing.

6. The UV-C light device of claim 5 including:
a plurality of apertures in the window allowing air to flow through the interior chamber of the housing.

* * * * *